United States Patent [19]

Le

[11] Patent Number: 5,191,134
[45] Date of Patent: * Mar. 2, 1993

[54] AROMATICS ALKYLATION PROCESS

[75] Inventor: Quang N. Le, Cherry Hill, N.J.

[73] Assignee: Mobil Oil Corporation, Fairfax, Va.

[*] Notice: The portion of the term of this patent subsequent to Jun. 2, 2009 has been disclaimed.

[21] Appl. No.: 732,264

[22] Filed: Jul. 18, 1991

[51] Int. Cl.$^5$ ................................................. C07C 2/64
[52] U.S. Cl. .................................... 585/446; 585/467; 585/468
[58] Field of Search ........................ 585/467, 468, 446

[56] References Cited

U.S. PATENT DOCUMENTS

| | | | |
|---|---|---|---|
| 3,884,835 | 5/1975 | Vaughan | 252/451 |
| 4,091,079 | 5/1978 | Vaughan | 423/328 |
| 4,211,665 | 7/1980 | Pellegrini, Jr. | 252/63 |
| 4,238,343 | 12/1980 | Pellegrini, Jr. | 585/24 |
| 4,301,316 | 11/1981 | Young | 585/455 |
| 4,570,027 | 2/1986 | Boucher et al. | 585/445 |
| 4,604,491 | 8/1986 | Dressler et al. | 585/25 |
| 4,673,559 | 6/1987 | Derouane et al. | 423/329 |
| 4,714,794 | 12/1987 | Yoshida et al. | 585/26 |
| 4,791,088 | 12/1988 | Chu et al. | 502/232 |
| 4,876,408 | 10/1989 | Ratcliffe et al. | 585/467 |
| 4,880,611 | 11/1989 | von Ballmoos et al. | 423/306 |
| 4,973,461 | 11/1990 | Vaughan | 502/66 |
| 4,962,256 | 10/1990 | Le et al. | 258/467 |
| 5,034,563 | 7/1991 | Ashjian et al. | 585/455 |
| 5,118,894 | 6/1992 | Le | 585/446 |

Primary Examiner—Asok Pal
Assistant Examiner—C. Everhart
Attorney, Agent, or Firm—Alexander J. McKillop; Dennis P. Santini; Malcolm D. Keen

[57] ABSTRACT

Long chain alkyl substituted aromatic compounds, particularly alkylated naphthalenes are produced by the alkylation of aromatics, e.g. naphthalene, with an olefin or other alkylating agent possessing at least 6 carbon atoms, usually 12 to 20 carbon atoms, in the presence of an alkylation catalyst which comprises a mesoporous crytalline material. The mesoporous material has pores with diameters of at least 13 Å which, in the preferred catalytic form, are arranged in a uniform hexagonal arrangement, and have a X-ray diffraction pattern with at least one d-spacing greater than about 18 Å. These materials exhibit benzene adsorption capacities greater than about 15 grams benzene per 100 grams at 50 torr and 25° C. In its preferred catalytic form, the crystalline material exhibits a hexagonal electron diffraction pattern that can be indexed with a $d_{100}$ value greater than about 18 Å which corresponds to at least one peak in the X-ray diffraction pattern.

30 Claims, No Drawings

AROMATICS ALKYLATION PROCESS

CROSS-REFERENCE TO RELATED APPLICATIONS

The mesoporous crystalline materials used in the catalysts in the present process are described in application Ser. No. 07/470,008, filed Jan. 25, 1990, (C. T. Kresge et al) which is a continuation-in-part of Ser. No. 07/625,425, filed Dec. 10, 1990 (C. T. Kresge et al).

FIELD OF THE INVENTION

This invention relates to the production of alkylated aromatics, especially of alkylated naphthalenes and substituted naphthalenes.

BACKGROUND OF THE INVENTION

Alkylaromatic fluids have been proposed for use as certain types of functional fluids where good thermal and oxidative stability are required. For example, U.S. Pat. No. 4,714,794 (Yoshida) describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491 (Dressler) and Pellegrini U.S. Pat. Nos. 4,211,665 and 4,238,343 describe the use of alkylaromatics as transformer oils.

The alkylated naphthalenes are usually produced by the alkylation of naphthalene or a substituted naphthalene in the presence of an acidic alkylation catalyst such as a Friedel-Krafts catalyst, for example, an acidic clay as described in Yoshida U.S. Pat. No. 4,714,794 or Dressler U.S. Pat. No. 4,604,491 or a Lewis acid such as aluminum trichloride as described in Pellegrini U.S. Pat. Nos. 4,211,665 and 4,238,343. The use of a catalyst described as a collapsed silica-alumina zeolite as the catalyst for the alkylation of aromatics such as naphthalene is disclosed in Boucher U.S. Pat. No. 4,570,027. The use of various zeolites including intermediate pore size zeolites such as ZSM-5 and large pore size zeolites such as zeolite L and ZSM-4 for the alkylation of various monocyclic aromatics such as benzene is disclosed in Young U.S. Pat. No. 4,301,316 and U.S. Pat. No. 4,962,256.

In the formulation of functional fluids based on the alkyl naphthalenes, it has been found that the mono-substituted naphthalenes are often preferred because they provide the best combination of properties in the finished product: there are fewer benzylic hydrogens than the corresponding di-substituted or polysubstituted versions and as a result, the mono-alkylated derivatives have better oxidative stability. The mono-substituted naphthalenes usually have a kinematic viscosity in the range of about 5–8 cSt (at 100° C.) when working with alkyl substituents of about 14 to 18 carbon atoms chain length and this means that they usually have to be blended with more viscous materials to produce the higher viscosity fluids. The mono-alkylated naphthalenes tend to be less stable than the corresponding polyalkylated derivatives but they do, nevertheless, have certain utilities. They have higher viscosities and can therefore be used for blending with the mono-alkylated materials for obtaining higher viscosity products; in addition, the presence of more alkyl groups tends to improve their viscosity index (VI), particularly when the alkyl groups are derived from high VI materials.

SUMMARY OF THE INVENTION

It has now been found that certain crystalline catalytic materials—the mesoporous crystalline solids—having a unique and novel crystalline structure are extremely effective catalysts for the production of alkylated aromatic compounds, especially alkylated naphthalenes.

According to the present invention, therefore, we provide a process for the production of alkylated aromatics by the alkylation of an aromatic compound, preferably a polycyclic aromatic such as naphthalene or a substituted naphthalene in the presence of an alkylation catalyst which comprises a mesoporous siliceous material. The mesoporous crystalline catalysts are notable for their ability to produce polyalkylated aromatics together with the lower alkylated products. These more highly alkylated products of higher molecular weight can contribute useful properties to the product, including higher viscosity, additive solvency and, depending on the alkylating agent, viscosity index.

The mesoporous crystalline materials which are used in the present process are materials are inorganic, porous, non-layered crystalline phase materials which, in their calcined forms exhibit an X-ray diffraction pattern with at least one peak at a d-spacing greater than about 18 Angstrom Units (Å) with a relative intensity of 100. They also have a benzene adsorption capacity greater than 15 grams benzene per 100 grams of the material at 50 torr and 25° C. In a preferred form, the catalytic material is characterized by a substantially uniform hexagonal honeycomb microstructure with uniform pores having a cell diameter greater than 13 Å and typically in the range of 20 to 100 Å.

Most prominent among these materials is a new crystalline material identified as MCM-41 which is usually synthesized as a metallosilicate with Brønsted acid sites by incorporating a tetrahedrally coordinated trivalent element such as Al, Ga, B, or Fe within the silicate framework. MCM-41 is characterized by a microstructure with a uniform, hexagonal arrangement of pores with diameters of at least about 13 Å: after calcination it exhibits an X-ray diffraction pattern with at least one d-spacing greater than about 18 Å with a relative intensity of 100, and a hexagonal electron diffraction pattern that can be indexed with a $d_{100}$ value greater than about 18 Å which corresponds to the d-spacing of the peak in the X-ray diffraction pattern. The preferred catalytic form of this material is the aluminosilicate although other metallosilicates may also be utilized.

The ability of the present class of catalysts to produce high viscosity, poly-alkylated naphthalene lubricants provides greater flexibility for various product applications. Furthermore the ultra-large pore size catalysts have the potential, as a result of their large pore dimensions, to functionalize (by aromatic alkylation) various high molecular weight olefin oligomers such as poly-alpha-olefins (PAO), high viscosity index PAO (HVI-PAO) for product quality improvement.

DETAILED DESCRIPTION

Aromatic Compound

The starting materials for the production of the alkyl-aromatic products include various aromatic compounds such as benzene and the low and high molecular weight alkylbenzenes, including low molecular weight alkylbenzenes such as toluene and the isomeric xylenes and mixtures of such materials. Higher molecular weight alkylbenzenes may be alkylated in this way as well as other aromatics including anthracene, phenanthrene and aromatics with other fused ring systems. The process is, however, of primary applicability with the production of alkylated naphthalenes since these products have been found to provide lubricant materials of very good stability which may be blended with other lubricant components such as the poly-alphaolefins. For convenience and brevity, the process is described below primarily with reference to the production of alkylated naphthalenes but it may also be used in a similar manner for the production of other alkylated aromatics.

The starting materials for the production of alkylated naphthalenes include naphthalene itself as well the substituted naphthalenes which may contain one or more short chain alkyl groups containing up to about eight carbon atoms, such as methyl, ethyl or propyl. Suitable alkyl-substituted naphthalenes include alpha-methylnaphthalene, dimethylnaphthalene and ethylnaphthalene. Naphthalene itself is preferred since the resulting mono-alkylated products have better thermal and oxidative stability than the more highly alkylated materials for the reasons set out above.

Alkylating Agents

The alkylating agents which are used to alkylate the aromatic compound include any aliphatic or aromatic organic compound having one or more available alkylating aliphatic groups capable of alkylating the naphthalene The alkylatable group itself should have at least about 6 carbon atoms, preferably at least about 8, and still more preferably at least about 12 carbon atoms. For the production of functional fluids and additives, the alkyl groups on the alkyl-naphthalene preferably have from about 12 to 30 carbon atoms, with particular preference to about 14 to 18 carbon atoms. A preferred class of alkylating agents are the olefins with the requisite number of carbon atoms, for example, the hexenes, heptenes, octenes, nonenes, decenes, undecenes, dodecenes. Mixtures of the olefins, e.g. mixtures of $C_{12}$–$C_{20}$ or $C_{14}$–$C_{18}$ olefins, are useful. Branched alkylating agents, especially oligomerized olefins such as the trimers, tetramers, pentamers, etc., of light olefins such as ethylene, propylene, the butylenes, etc., are also useful. Other useful alkylating agents which may be used, although less easily, include alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and higher homologs.

A particularly useful class of alkylating agents are the poly-alpha-olefins produced by the oligomerization of alpha-olefins. Commercial products of this kind are widely available and are usually produced by the oligomerization of 1-olefins such as 1-decene over a Friedel-Crafts catalyst such as aluminum trichloride, boron trifluoride or its complexes e.g. with alcohols or esters. These materials are usually liquids ranging in viscosity from mobile (5 cS or lower) up to viscous semi-liquids. Products of this type may be used as alkylating agents in the present process because the pore structure of the mesoporous alkylation catalysts used in the process is able to accommodate these species even when they have high molecular weight and bulky molecular dimensions, enabling the alkylation reaction to occur and facilitating the production of alkylated products with a wide range of varying properties.

A particularly favored class of PAO alkylating agents are the HVI-PAO products. These olefin oligomers are produced by the oligomerization of alpha-olefins such as 1-decene over a reduced Group VI metal catalyst, especially reduced chromium catalysts. The HVI-PAO olefin oligomers are characterized by a low branch ratio of less than 0.19 as well as by other properties such as low pour point. HVI-PAO materials are described in U.S. Pat. Nos. 4,827,064 and 4,827,073, to which reference is made for a description of such products and of their preparation, as well as of the significance of the branch ratio of these materials.

Alkylation Catalyst

The alkylation reaction is carried out in the presence of a solid, mesoporous acidic catalytic material which a characteristic structure and other properties described below.

The catalytic material used in the present invention includes a novel synthetic composition of matter comprising an ultra-large pore size crystalline phase. This material is an inorganic, porous, non-layered crystalline phase material which can be characterized (in its calcined form) by an X-ray diffraction pattern with at least one peak at a d-spacing greater than about 18 Å with a relative intensity of 100 and a benzene sorption capacity of greater than 15 grams of benzene per 100 grams of the material at 50 torr and 25° C.

The preferred form of the crystalline material is an inorganic, porous, non-layered material having a hexagonal arrangement of uniformly-sized pores with a maximum perpendicular cross-section pore dimension of at least about 13 Angstron Units (Å), and typically within the range of from about 13 Å to about 200 Å. A preferred form of this catalytic material is the aluminosilicate hexagonal crystalline composition, identified as MCM-41, with the characteristic structure of hexagonally-arranged, uniformly-sized pores of at least 13 Å diameter. This material exhibits a hexagonal electron diffraction pattern that can be indexed with a $d_{100}$ value greater than about 18 Å which corresponds to at least one peak in the X-ray diffraction pattern. The preferred catalytic materials are described in application Ser. No. 07/625,425 and also below.

The inorganic, non-layered mesoporous crystalline materials used as a component of the catalyst have the following composition:

$$M_{n/q}(W_aX_bY_cZ_dO_h)$$

where W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1.

A preferred embodiment of the crystalline material is when (a+b+c) is greater than d, and h=2. A further embodiment is when a and d=0, and h=2. The preferred materials for use in making the present catalysts are the aluminosilicates although other metallosilicates may also be used.

In the as-synthesized form, the support material has a composition, on an anhydrous basis, expressed empirically as follows:

$$rRM_{n/q}(W_aX_bY_cZ_dO_h)$$

where R is the total organic material not included in M as an ion, and r is the coefficient for R, i.e. the number of moles or mole fraction of R.

The M and R components are associated with the material as a result of their presence during crystallization, and are easily removed or, in the case of M, replaced by post-crystallization methods described below.

To the extent desired, the original M, e.g. sodium or chloride, ions of the as-synthesized material of this invention can be replaced in accordance with conventional ion-exchange techniques. Preferred replacing ions include metal ions, hydrogen ions, hydrogen precursor, e.g. ammonium, ions and mixtures of these ions. Particularly preferred ions are those which provide the desired metal functionality in the final catalyst. These include hydrogen, rare earth metals and metals of Groups VIIA (e.g. Mn), VIIIA (e.g. Ni), IB (e.g. Cu), IVB (e.g. Sn) of the Periodic Table of the Elements and mixtures of these ions. When it is used in the present catalysts, the mesoporus crystalline material is at least partly in the hydrogen form in order to provide the acidic functionality for the alkylation reaction.

The crystalline (i.e. having sufficient order to provide a diffraction pattern such as, for example, by X-ray, electron or neutron diffraction, following calcination with at least one peak) mesoporous material may be characterized by its structure, which includes extremely large pore windows as well as by its high sorption capacity. The term "mesoporous" is used here to indicate crystals having uniform pores within the range of from about 13 Å to about 200 Å. The mesoporous materials have uniform pores within the range of from about 13 Å to about 200 Å, more usually from about 15 Å to about 100 Å. Since these pores are significantly larger than those of other crystalline materials, it is appropriate to refer to them as ultra-large pore size materials. For the purposes of this application, a working definition of "porous" is a material that adsorbs at least 1 gram of a small molecule, such as Ar, $N_2$, n-hexane or cyclohexane, per 100 grams of the solid.

The catalytic material can be distinguished from other porous inorganic solids by the regularity of its large open pores, whose pore size more nearly resembles that of amorphous or paracrystalline materials, but whose regular arrangement and uniformity of size (pore size distribution within a single phase of, for example, ±25%, usually ±15% or less of the average pore size of that phase) resemble more those of crystalline framework materials such as zeolites. The preferred materials have a hexagonal arrangement of large open channels that can be synthesized with open internal diameters from about 13 Å to about 200 Å. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as ±25% random deviation from the average repeat distance between adjacent channels still clearly give recognizable images of the present ultra-large pore materials. Comparable variations are also observed in the $d_{100}$ values from the electron diffraction patterns.

The most regular preparations of the material of the present invention give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the material. The most highly ordered preparations of the material obtained so far have 20–40 distinct spots observable in the electron diffraction patterns. These patterns can be indexed with the hexagonal hk0 subset of unique reflections of 100, 110, 200, 210, etc., and their symmetry-related reflections.

In its calcined form, the crystalline material may be further characterized by an X-ray diffraction pattern with at least one peak at a position greater than about 18 Angstrom Units d-spacing (4.909° 2θ for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials, e.g. silica, and organics may be removed by contact with acid or base or other chemical agents such that the detrital material will be removed without detrimental effect on the crystal.

More particularly, the calcined crystalline non-layered material may be characterized by an X-ray diffraction pattern with at least two peaks at positions greater than about 10 Å d-spacing (8.842°$\theta$ for Cu K-alpha radiation), at least one of which is at a position greater than about 18 Å d-spacing, and no peaks at positions less than about 10 Å d-spacing with relative intensity greater than about 20% of the strongest peak. Still more particularly, the X-ray diffraction pattern of the calcined material of this invention will have no peaks at positions less than about 10 Å d-spacing with relative intensity greater than about 10% of the strongest peak. In any event, at least one peak in the X-ray diffraction pattern will have a d-spacing that corresponds to the $d_{100}$ value of the electron diffraction pattern of the material.

The calcined inorganic, non-layered crystalline material may also be characterized as having a pore size of about 13 Å or greater as measured by physisorption measurements, described below. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of $2\theta$, where $\theta$ is the Bragg angle, and a counting time of 10 seconds for each step. The interplanar spacings, d's, were calculated in Å (A), and the relative intensities of the lines, $I/I_0$, where $I_0$ is one-hundredth of the intensity of the strongest line, above background, were derived with the use of a profile fitting routine. The intensities were uncorrected for Lorentz and polarization effects. The relative intensities are given in terms of the symbols vs=very strong (75-100), s=strong (50-74), m=medium (25-49) and w=weak (0-24). The diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the material of the invention, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as described below.

The ammonium form of the catalytic material may be readily converted to the hydrogen form by thermal treatment (calcination). This thermal treatment is generally performed by heating one of these forms at a temperature of at least 400° C. for at least 1 minute and generally not longer than 20 hours, preferably from about 1 to about 10 hours. Because the alkylation reaction requires the alkylation catalyst to possess acidic activity and for this reason the mesoporous material will be at least partly in the hydrogen form for use in the present process. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

The mesoporous crystalline material can be prepared by one of several methods, each with particular limitations.

A first method involves a reaction mixture having an $X_2O_3/YO_2$ mole ratio of from 0 to about 0.5, but an $Al_2O_3SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, described below. This first method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, an organic (R) directing agent, described below, and a solvent or solvent mixture, such as, for example, $C_1$-$C_6$ alcohols, $C_1$-$C_6$ diols and/or water, especially water. The reaction mixture has a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $Al_2O_3/SiO_2$ | 0 to 0.01 | 0.001 to 0.01 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/ $(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/ (YO_2 + WO + Z_2O_5 + X_2O_3)$ | 0.01 to 20 | 0.05 to 5 |
| $M_{2/e}O/ (YO_2 + WO + Z_2O_5 + X_2O_3)$ | 0 to 10 | 0 to 5 |
| $R_{2/f}O/ (YO_2 + WO + Z_2O_5 + X_2O_3)$ | 0.01 to 2.0 | 0.03 to 1.0 | where e and f are the weighted average valences of M and R, respectively.

In this first method, when no Z and/or W oxides are added to the reaction mixture, the pH is important and must be maintained at from about 9 to about 14. When Z and/or W oxides are present in the reaction mixture, the pH is not narrowly important for synthesis of the present crystalline material. In this, as well as the following methods for synthesis of the present material the $R_{2/f}O/(YO_2+WO+Z_2O_5+X_2O_3)$ ratio is important. When this ratio is less than 0.01 or greater than 2.0, impurity products tend to be synthesized at the expense of the desired crystalline material.

A second method for synthesis of the crystalline material involves a reaction mixture having an $X_2O_3/YO_2$ mole ratio of from about 0 to about 0.5, a crystallization temperature of from about 25° C. to about 250° C., preferably from about 50° C. to about 175° C., and two separate organic directing agents, i.e. the organic and additional organic directing agents, described below. This second method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, a combination of organic directing agent and additional organic directing agent (R), each described below, and a solvent or solvent mixture, such as, for example, $C_1-C_6$ alcohols, $C_1-C_6$ diols and/or water, especially water. The reaction mixture has a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/ $(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.1 to 2.0 | 0.12 to 1.0 | where e and f are the weighted average valences of M and R, respectively.

In this second method, when no Z and/or W oxides are added to the reaction mixture, the pH is important and must be maintained at from about 9 to about 14. When Z and/or W oxides are present in the reaction mixture, the precise value of the pH is not important for crystallization.

A third method for synthesis of the crystalline material is where X comprises aluminum and Y comprises silicon, the crystallization temperature must be from about 25° C. to about 175° C., preferably from about 50° C. to about 150° C., and an organic directing agent, described below, or, preferably a combination of that organic directing agent plus an additional organic agent, described below, is used. This third method comprises preparing a reaction mixture containing sources of, for example, alkali or alkaline earth metal (M), e.g. sodium or potassium, cation if desired, one or more sources of aluminum and/or silicon, an organic (R) directing agent, hereinafter more particularly described, and a solvent or solvent mixture, such as, for example $C_1-C_6$ alcohols, $C_1-C_6$ diols and/or water, especially water. The reaction mixture has a composition, in terms of mole ratios of oxides, within the following ranges:

| Reactants | Useful | Preferred |
|---|---|---|
| $Al_2O_3/SiO_2$ | 0 to 0.5 | 0.001 to 0.5 |
| Solvent/$SiO_2$ | 1 to 1500 | 5 to 1000 |
| $OH^-/SiO_2$ | 0 to 10 | 0 to 5 |
| $(M_{2/e}O + R_{2/f}O)/(SiO_2 + Al_2O_3)$ | 0.01 to 20 | 0.05 to 5 |
| $M_{2/e}O/(SiO_2 + Al_2O_3)$ | 0 to 5 | 0 to 3 |
| $R_{2/f}O/(SiO_2 + Al_2O_3)$ | 0.01 to 2 | 0.03 to 1 | where e and f are the weighted average valences of M and R, respectively.

In this third method, the pH is important and must be maintained at from about 9 to about 14. This method involves the following steps:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) To the primary template mixture of step (1) add the sources of oxides, e.g. silica and/or alumina such that the ratio of $R_{2/f}O/(SiO_2+Al_2O_3)$ is within the range of from about 0.01 to about 2.0.

(3) Agitate the mixture resulting from step (2) at a temperature of from about 20° C. to about 40° C., preferably for from about 5 minutes to about 3 hours.

(4) Allow the mixture to stand with or without agitation, preferably at a temperature of from about 20° C. to about 100° C., and preferably for from about 10 minutes to about 24 hours.

(5) Crystallize the product from step (4) at a temperature of from about 50° C. to about 175° C., preferably for from about 1 hour to about 72 hours. Crystallization temperatures higher in the given ranges are most preferred.

A fourth method for the present synthesis involves the reaction mixture used for the third method, but the following specific procedure with tetraethylorthosilicate the source of silicon oxide:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) Mix the primary template mixture of step (1) with tetraethylorthosilicate and a source of aluminum oxide, if desired, such that the $R_{2/f}O/SiO_2$ mole ratio is in the range of from about 0.5 to about 2.0.

(3) Agitate the mixture resulting from step (2) for from about 10 minutes to about 6 hours, preferably from about 30 minutes to about 2 hours, at a temperature of from about 0° C. to about 25° C., and a pH of less than 12. This step permits hydrolysis/polymerization to take place and the resultant mixture will appear cloudy.

(4) Crystallize the product from step (3) at a temperature of from about 25° C. to about 150° C., preferably from about 95° C. to about 110° C., for from about 4 to about 72 hours, preferably from about 16 to about 48 hours.

In each of the above methods, batch crystallization of the crystalline material can be carried out under either static or agitated, e.g. stirred, conditions in a suitable reactor vessel, such as for example, polypropylene jars or teflon lined or stainless steel autoclaves. Crystallization may also be conducted continuously in suitable equipment. The total useful range of temperatures for crystallization is noted above for each method for a time sufficient for crystallization to occur at the temperature used, e.g. from about 5 minutes to about 14 days. The crystals are then separated from the liquid and recovered. Following the synthesis, the crystalline material should be subjected to treatment to remove part or all of any organic constituent.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

By adjusting conditions of the synthesis reaction for each method, like temperature, pH and time of reaction, etc., within the above limits, various embodiments of the present non-layered crystalline material with a desired average pore size may be prepared. In particular, changing the pH, the temperature or the reaction time may promote formation of product crystals with different average pore size.

Non-limiting examples of various combinations of W, X, Y and Z contemplated for the first and second synthesis methods include:

| W  | X  | Y  | Z |
|----|----|----|---|
| —  | Al | Si | — |
| —  | Al | —  | P |
| —  | Al | Si | P |
| Co | Al | —  | P |
| Co | Al | Si | P |
| —  | —  | Si | — | including the combinations of W being Mg, or an element selected from the divalent first row transition metals, e.g. Mn, Co and Fe; X being B, Ga or Fe; and Y being Ge.

An organic directing agent for use in each of the above methods for synthesizing the present material from the respective reaction mixtures is an ammonium or phosphonium ion of the formula $R_1R_2R_3R_4Q^+$, i.e.:

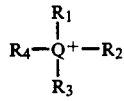

where Q is nitrogen or phosphorus and wherein at least one of $R_1$, $R_2$, $R_3$ and $R_4$ is aryl or alkyl of from 6 to about 36 carbon atoms, e.g. $-C_6H_{13}$, $-C_{10}H_{21}$, $-C_{16}H_{33}$ and $-C_{18}H_{37}$, or combinations thereof, the remainder of $R_1$, $R_2$, $R_3$ and $R_4$ being selected from hydrogen, alkyl of from 1 to 5 carbon atoms and combinations of these. The compound from which the above ammonium or phosphonium ion is derived may be, for example, the hydroxide, halide, silicate, or mixtures of these.

In the first and third methods above it is preferred to have an additional organic directing agent and in the second method it is required to have a combination of the above organic directing agent and an additional organic directing agent. That additional organic directing agent is the ammonium or phosphonium ion of the above directing agent formula wherein $R_1$, $R_2$, $R_3$ and $R_4$ together or separately are selected from the group consisting of hydrogen and alkyl of 1 to 5 carbon atoms and combinations thereof. Any such combination of organic directing agents go to make up "R" and will be in molar ratio of about 100/1 to about 0.01/1, first above listed organic directing agent/additional organic directing agent.

The particular effectiveness of the required directing agent, when compared with other such agents known to direct synthesis of one or more other crystal structures, is believed due to its ability to function as a template in the above reaction mixture in the nucleation and growth of the desired ultra-large pore crystals with the limitations discussed above. Non-limiting examples of these directing agents include cetyltrimethylammonium, cetyltrimethylphosphonium, benzyltrimethylammonium, cetylpyridinium, myristyltrimethylammonium, decyltrimethylammonium, dodecyltrimethylammonium and dimethyldidodecylammonium.

The reaction mixture components can be supplied by more than one source. The reaction mixture can be prepared either batchwise or continuously. Crystal size and crystallization time of the new crystalline material will vary with the nature of the reaction mixture employed and the crystallization conditions.

The crystals prepared by the synthesis procedure can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The size of the pores in the present mesoporous catalytic materials is large enough that the spatiospecific selectivity with respect to transition state species in reactions such as cracking is minimized (Chen et al., "Shape Selective Catalysis in Industrial Applications", 36 CHEMICAL INDUSTRIES, pgs. 41–61 (1989) to which reference is made for a discussion of the factors affecting shape selectivity). Diffusional limitations are also minimized as a result of the very large pores.

The crystals of the mesoporous support material will normally be composited with a matrix material which is resistant to the temperatures and other conditions employed in the alkylation process to form the finished catalyst. Such materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that alkylation products can be obtained economically and orderly without employing other means for controlling the rate of reaction. These materials may be incorporated into naturally occurring clays, e.g., bentonite and kaolin, to improve the crush strength of the catalyst under commercial alkylation operating conditions and function as binders or matrices for the catalyst. The mesoporous material is usually composited with the matrix in amounts from 80:20 to 20:80 by weight, typically from 80:20 to 50:50 mesoporous material:matrix. Compositing may be done by conventional means including mulling the materials together followed by extrusion of pelletizing into the desired finished catalyst particles.

Alkylation Conditions

The alkylation is conducted such that the organic reactants, i.e., the alkylatable aromatic compound and the alkylating agent, are brought into contact with the catalyst in a suitable reaction zone such as, for example, in a batch type reactor or flow reactor containing a fixed bed of the catalyst composition, under effective alkylation conditions. Such conditions typically include a temperature of from about 100° C. to about 400° C., a pressure of from about 0.2 to about 250 atmospheres, a feed weight hourly space velocity (WHSV) of from about 0.1 hr$^{-1}$ to about 10 hr$^{-1}$ and an alkylatable aromatic compound to alkylating agent mole ratio of from about 0.1:1 to about 50:1, preferably from about 4:1 to about 1:4 e.g. from about 2:1 to about 1:2.

In a continous, fixed bed type operation, the temperature will normally be in the range 200° to 600° F. (about 93° to 315° C.), preferably 300° to 400° F. (about 150° to about 205° C.), with pressures in the range of 50 to 1000 psig (about 450 to about 7,000 kPa abs). The WHSV is based upon the weight of the catalyst composition employed, i.e., the total weight of active catalyst (and binder if present) and is normally in the range of 0.1 to 5.0, preferably 0.5 to 5.0, with most cases in the range 0.25 to 1.50. Preferred reaction conditions include a temperature within the approximate range of from about 100° to about 350° C., a pressure of from about 1 to about 25 atmospheres, a WHSV of from about 0.5 hr$^{-1}$ to about 5 hr$^{-1}$ and an alkylatable aromatic compound to alkylating agent mole ratio of from about 0.5:1 to about 5:1.

When using naphthalene as the aromatic compound, the pressure should preferably be maintained at a value of at least about 50 psig in order to prevent the naphthalene from subliming into the overhead of the alkylation reactor; the required pressure may be maintained by inert gas pressurization, preferably with nitrogen. The reactants can be in either the vapor phase or the liquid phase and can be neat, i.e., free from intentional admixture or dilution with other material, or they can be brought into contact with the catalyst with the aid of carrier gases or diluents such as, for example, hydrogen or nitrogen. The alkylation can be carried out as a batch-type reaction typically employing a closed, pressurized, stirred reactor with an inert gas blanketing system or in a semi-continuous or continuous operation utilizing a fixed or moving bed catalyst system.

The products comprising alkylated aromatics are characterized by exceptional oxidative and thermal stability. They may be separated from the reaction mixture by stripping off unreacted alkylating agent and naphthalene compound in the conventional manner. It has also been found that the stability of the alkylated product may be improved by filtration over activated charcoal and by alkali treatment to remove impurities, especially acidic by-products formed by oxidation during the course of the reaction. The alkali treatment is preferably carried out by filtration over a solid alkali material, preferably calcium carbonate (lime).

EXAMPLES

Examples 1 to 19 below illustrate the preparation of the mesoporous crystalline materials used to prepare the catalysts. In these examples, the sorption data for water, cyclohexane, benzene and/or n-hexane, they are Equilibrium Adsorption values determined as follows:

A weighed sample of the adsorbent, after calcination at about 540° C. for at least about 1 hour and other treatment, if necessary, to remove any pore blocking contaminants, is contacted with the desired pure adsorbate vapor in an adsorption chamber. The increase in weight of the adsorbent is calculated as the adsorption capacity of the sample in terms of grams/100 grams adsorbent based on adsorbent weight after calcination at about 540° C. The present composition exhibits an equilibrium benzene adsorption capacity at 50 Torr and 25° C. of greater than about 15 grams/100 grams, particularly greater than about 17.5 g/100 g/ and more particularly greater than about 20 g/100 g.

A preferred way to do this is to contact the desired pure adsorbate vapor in an adsorption chamber evacuated to less than 1 mm at conditions of 12 Torr of water vapor, 40 Torr of n-hexane or cyclohexane vapor, or 50 Torr of benzene vapor, at 25° C. The pressure is kept constant (within about ±0.5 mm) by addition of adsorbate vapor controlled by a manostat during the adsorption period. As adsorbate is adsorbed by the new crystal, the decrease in pressure causes the manostat to open a valve which admits more adsorbate vapor to the chamber to restore the above control pressures. Sorption is complete when the pressure change is not sufficient to activate the manostat.

Another way of doing this for benzene adsorption data is on a suitable thermogravimetric analysis system, such as a computer-controlled 990/951 duPont TGA system. The adsorbent sample is dehydrated (physically sorbed water removed) by heating at, for example, about 350° C. or 500° C. to constant weight in flowing helium. If the sample is in as-synthesized form, e.g. containing organic directing agents, it is calcined at about 540° C. in air and held to constant weight instead of the previously described 350° C. or 500° C. treatment. Benzene adsorption isotherms are measured at 25° C. by blending a benzene saturated helium gas stream with a pure helium gas stream in the proper proportions to obtain the desired benzene partial pressure. The value of the adsorption at 50 Torr of benzene is taken from a plot of the adsorption isotherm.

In the examples, percentages are by weight unless otherwise indicated.

EXAMPLE 1

One hundred grams of cetyltrimethylammonium (CTMA) hydroxide solution, prepared by contacting a 29 wt. % N,N,N-trimethyl-1-hexadecanaminium chloride solution with a hydroxide-for-halide exchange resin, was combined with 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a polypropylene bottle, which was placed in a steam box at 95° C. overnight. The mixture had a composition in terms of moles per mole $Al_2O_3$:

2.7 moles Na$_2$O 392 moles SiO$_2$ 35.7 moles (CTMA)$_2$O 61.7 moles (TMA)$_2$O 6231 moles H$_2$O The resulting solid product was recovered by filtration and dried in air at ambient temperature. The product was then calcined at 540° C. for 1 hour in nitrogen, followed by 6 hours in air.

The calcined product proved to have a surface area of 475 m$^2$/g and the following equilibrium adsorption capacities in grams/100 grams:

| | |
|---|---|
| H$_2$O | 8.3 |
| Cyclohexane | 22.9 |
| n-Hexane | 18.2 |
| Benzene | 21.5 |

The product of this example may be characterized by X-ray diffraction as including a very strong relative intensity line at 37.8±2.0 Å d-spacing, and weak lines at 21.6±1.0 and 19.2±1.0 Å. Transmission electron microscopy (TEM) produced images of a hexagonal arrangement of uniform pores and hexagonal electron diffraction pattern with a d$_{100}$ value of about 39 Å.

EXAMPLE 2

One hundred grams of cetyltrimethylammonium (CTMA) hydroxide solution prepared as in Example 1 was combined with 100 grams of an aqueous solution of tetramethylammonium (TMA) hydroxide (25%) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. overnight. The mixture had a composition in terms of moles per mole Al$_2$O$_3$:

2.7 moles Na$_2$O 291 moles SiO$_2$ 35.7 moles (CTMA)$_2$O 102 moles (TMA)$_2$O 6120 moles H$_2$O The resulting solid product was recovered by filtration and dried in air at ambient temperature. The product was then calcined at 540° C. for 1 hour in nitrogen, followed by 6 hours in air.

The calcined product proved to have a surface area of 993 m$^2$/g and the following equilibrium adsorption capacities in grams/100 grams:

| | |
|---|---|
| H$_2$O | 7.1 |
| Cyclohexane | 47.2 |
| n-Hexane | 36.2 |
| Benzene | 49.5 |

The X-ray diffraction pattern of the calcined product may be characterized as including a very strong relative intensity line at 39.3±2.0 Å d-spacing, and weak lines at 22.2±1.0 and 19.4±1.0 Å. TEM indicated that the product contained the ultra-large pore material.

A portion of the above product was then contacted with 100% steam at 1450° F. for two hours. The surface area of the steamed material was measured to be 440 m$^2$/g, indicating that about 45% was retained following severe steaming.

Another portion of the calcined product of this example was contacted with 100% steam at 1250° F. for two hours. The surface area of this material was measured to be 718 m$^2$/g, indicating that 72% was retained after steaming at these conditions.

EXAMPLE 3

Water, cetyltrimethylammonium hydroxide solution prepared as in Example 1, aluminum sulfate, HiSil and an aqueous solution of tetrapropylammonium (TPA) bromide (35%) were combined to produce a mixture having a composition in terms of moles per mole Al$_2$O$_3$:

0.65 moles Na$_2$O 65 moles SiO$_2$ 8.8 moles (CTMA)$_2$O 1.22 moles (TPA)$_2$O 1336 moles H$_2$O The resulting mixture was placed in a polypropylene bottle, which was kept in a steam box at 95° C. for 192 hours. The sample was then cooled to room temperature and combined with CTMA hydroxide solution prepared as in Example 1 and TMA hydroxide (25% by weight) in the weight ratio of 3 parts mixture, 1 part CTMA hydroxide and 2 parts TMA hydroxide. The combined mixture was then placed in a polypropylene bottle and kept in a steam box at 95° C. overnight. The combined mixture had a composition in terms of moles per mole Al$_2$O$_3$:

0.65 moles Na$_2$O 65 moles SiO$_2$ 15 moles (CTMA)$_2$O 1.22 moles (TPA)$_2$O 35.6 moles (TMA)$_2$O 2927 moles H$_2$O The resulting solid product was recovered by filtration and dried in air at ambient temperature. The product was then calcined at 540° C. for 1 hour in nitrogen, followed by 6 hours in air.

The calcined product proved to have a surface area of 1085 m$^2$/g and the following equilibrium adsorption capacities in grams/100 grams:

| | |
|---|---|
| H$_2$O | 11.5 |
| Cyclohexane | >50 |
| n-Hexane | 39.8 |
| Benzene | 62 |

The X-ray diffraction pattern of the calcined product of this example may be characterized as including a very strong relative intensity line at 38.2±2.0 Å d-spacing, and weak lines at 22.2±1.0 and 19.4±1.0 Å. TEM indicated the product contained the ultra-large pore material.

EXAMPLE 4

Two hundred grams of cetyltrimethylammonium (CTMA) hydroxide solution prepared as in Example 1 was combined with 2 grams of Catapal alumina (alpha-alumina monohydrate, 74% alumina) and 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 48 hours. The mixture had a composition in terms of moles per mole $Al_2O_3$:

0.23 moles $Na_2O$ 33.2 moles $SiO_2$ 6.1 moles $(CTMA)_2O$ 5.2 moles $(TMA)_2O$ 780 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 1043 m²/g and the following equilibrium adsorption capacities in grams/100 grams:

| $H_2O$ | 6.3 |
| Cyclohexane | >50 |
| n-Hexane | 49.1 |
| Benzene | 66.7 |

The X-ray diffraction pattern of the calcined product may be characterized as including a very strong relative intensity line at 40.8±2.0 Å d-spacing, and weak lines at 23.1±1.0 and 20.1±1.0 Å. TEM indicated that the product contained the ultra-large pore material.

EXAMPLE 5

Two-hundred sixty grams of water was combined with 77 grams of phosphoric acid (85%), 46 grams of Catapal alumina (74% alumina), and 24 grams of pyrrolidine (Pyr) with stirring. This first mixture was placed in a stirred autoclave and heated to 150° C. for six days. The material was filtered, washed and air-dried. Fifty grams of this product was slurried with 200 grams of water and 200 grams of cetyltrimethylammonium hydroxide solution prepared as in Example 1. Four hundred grams of an aqueous solution of tetraethylammonium silicate (10% silica) was then added to form a second mixture which was placed in a polypropylene bottle and kept in a steam box at 95° C. overnight. The first mixture had a composition in terms of moles per mole $Al_2O_3$:

1.0 mole $P_2O_5$ 0.51 moles $(Pyr)_2O$ 47.2 moles $H_2O$

The resulting solid product was recovered by filtration and dried in air at ambient temperature. The product was then calcined at 540° C. for 1 hour in nitrogen, followed by 6 hours in air.

The calcined product proved to have a surface area of 707 m²/g and the following equilibrium adsorption capacities in grams/100 grams:

| $H_2O$ | 33.2 |
| Cyclohexane | 19.7 |
| n-Hexane | 20.1 |
| Benzene | 23.3 |

The X-ray diffraction pattern of the calcined product may be characterized as including a very strong relative intensity line at 25.4±1.5 Å d-spacing. TEM indicated the product contained the present ultra-large pore material.

EXAMPLE 6

A solution of 1.35 grams of $NaAlO_2$ (43.5% $Al_2O_3$, 30% $Na_2O$) dissolved in 45.2 grams of water was mixed with 17.3 grams of NaOH, 125.3 grams of colloidal silica (40%, Ludox HS-40) and 42.6 grams of 40% aqueous solution of tetraethylammonium (TEA) hydroxide. After stirring overnight, the mixture was heated for 7 days in a steam box (95° C.). Following filtration, 151 grams of this solution was mixed with 31 grams of cetyltrimethylammonium hydroxide solution prepared as in Example 1 and stored in the steam box at 95° C. for 13 days. The mixture had the following relative molar composition:

0.25 moles $Al_2O_3$ 10 moles $Na_2O$ 36 moles $SiO_2$ 0.95 moles $(CTMA)_2O$ 2.5 moles $(TEA)_2O$ 445 moles $H_2O$ The resulting solid product was recovered by filtration and washed with water and ethanol. The product was then calcined at 540° C. for 1 hour in nitrogen, followed by 6 hours in air.

The calcined product composition included 0.14 wt. % Na, 68.5 wt. % $SiO_2$ and 5.1 wt. % $Al_2O_3$, and proved to have a benzene equilibrium adsorption capacity of 58.6 grams/100 grams.

The X-ray diffraction pattern of the calcined product may be characterized as including a very strong relative intensity line at 31.4±1.5 Å d-spacing. TEM indicated that the product contained the present ultra-large pore material.

EXAMPLE 7

A mixture of 300 grams of cetyltrimethylammonium (CTMA) hydroxide solution prepared as in Example 1 and 41 grams of colloidal silica (40%, Ludox HS-40)

was heated in a 600 cc autoclave at 150° C. for 48 hours with stirring at 200 rpm. The mixture has a composition in terms of moles per mole $SiO_2$:

0.5 mole $(CTMA)_2O$ 46.5 moles $H_2O$

The resulting solid product was recovered by filtration, washed with water, then calcined at 540° C. for 1 hour in nitrogen, followed by 10 hours in air.

The calcined product composition included less than 0.01 wt. % Na, about 98.7 wt. % $SiO_2$ and about 0.01 wt. % $Al_2O_3$, and proved to have a surface area of 896 $m^2/g$. The calcined product had the following equilibrium adsorption capacities in grams/100 grams:

| | |
|---|---|
| $H_2O$ | 8.4 |
| Cyclohexane | 49.8 |
| n-Hexane | 42.3 |
| Benzene | 55.7 |

The X-ray diffraction pattern of the calcined product of this example may be characterized as including a very strong relative intensity line at 40.0±2.0 Å d-spacing and a weak line at 21.2±1.0 Å. TEM indicated that the product of this example contained at least three separate phases, one of which was the ultra-large pore material.

EXAMPLE 8

A mixture of 150 grams of cetyltrimethylammonium (CTMA) hydroxide solution prepared as in Example 1 and 21 grams of colloidal silica (40%, Ludox HS-40) with an initial pH of 12.64 was heated in a 300 cc autoclave at 150° C. for 48 hours with stirring at 200 rpm. The mixture had a composition in terms of moles per mole $SiO_2$:

0.5 mole $(CTMA)_2O$ 46.5 moles $H_2O$

The resulting solid product was recovered by filtration, washed with water, then calcined at 540° C. for 6 hours in air.

The calcined product composition was measured to include 0.01 wt. % Na, 93.2 wt. % $SiO_2$ and 0.016 wt. % $Al_2O_3$, and proved to have a surface area of 992 $m^2/g$ and the following equilibrium adsorption capacities in grams/100 grams:

| | |
|---|---|
| $H_2O$ | 6.3 |
| Cyclohexane | >50 |
| n-Hexane | >50 |
| Benzene | 66.7 |

The X-ray diffraction pattern of the calcined product may be characterized as including a very strong relative intensity line at 43.6±2.0 Å d-spacing and weak lines at 25.1±1.5 and 21.7±1.0 Å. TEM indicated that the product contained the ultra-large pore material.

EXAMPLE 9

Sodium aluminate (4.15 g) was added slowly into a solution containing 16 g of myristyltrimethylammonium bromide ($C_{14}TMABr$) in 100 g of water. Tetramethylammonium silicate (100 g-10% $SiO_2$), HiSil (25 g) and tetramethylammonium hydroxide (14.2 g-25% solution) were then added to the mixture. The mixture was crystallized in an autoclave at 120° C. with stirring for 24 hours.

The product was filtered, washed and air dried. Elemental analysis showed the product contained 53.3 wt % $SiO_2$, 3.2 wt % $Al_2O_3$, 15.0 wt % C, 1.88 wt % N, 0.11 wt % Na and 53.5 wt % ash at 1000° C. The X-ray diffraction pattern of the material after calcination at 540° C. for 1 hour in $N_2$ and 6 hours in air includes a very strong relative intensity line at 35.3±2.0 Å d-spacing and weak lines at 20.4±1.0 and 17.7±1.0 Å d-spacing. TEM indicated that the product contained the ultra-large pore material.

The washed product, having been exchanged with 1N ammonium nitrate solution at room temperature, then calcined, proved to have a surface area of 827 $m^2/g$ and the following equilibrium adsorption capacities in g/100 g anhydrous sorbent:

| | |
|---|---|
| $H_2O$ | 30.8 |
| Cyclohexane | 33.0 |
| n-Hexane | 27.9 |
| Benzene | 40.7 |

EXAMPLE 10

Sodium aluminum (4.15 g) was added slowly into a solution containing 480 g of dodecyltrimethylammonium hydroxide ($C_{12}TMAOH$, 50%) solution diluted with 120 g of water. UltraSil (50 g) and an aqueous solution of tetramethylammonium silicate (200 g-10% $SiO_2$) and tetramethylammonium hydroxide (26.38 g-25% solution) were then added to the mixture. The mixture was crystallized in an autoclave at 100° C. with stirring for 24 hours.

The product was filtered, washed and air dried. After calcination at 540° C. for 1 hour in $N_2$ and 6 hours in air, the X-ray diffraction pattern includes a very strong relative intensity line at 30.4±1.5 Å d-spacing and weak lines at 17.7±1.0 and 15.3±1.0 Å d-spacing. TEM indicated that the product contained the ultra-large pore material.

The washed product, having been exchanged with 1 N ammonium nitrate solution at room temperature, then calcined, proved to have a surface area of 1078 $m^2/g$ and the following equilibrium adsorption capacities in g/100 g anhydrous sorbent:

| | |
|---|---|
| $H_2O$ | 32.6 |
| Cyclohexane | 38.1 |
| n-Hexane | 33.3 |
| Benzene | 42.9 |

EXAMPLE 11

A solution of 4.9 grams of $NaAlO_2$ (43.5 % $Al_2O_3$, 30% $NaO_2$) in 37.5 grams of water was mixed with 46.3 cc of 40% aqueous tetraethylammonium hydroxide solution and 96 grams of colloidal silica (40%, Ludox HS-40). The gel was stirred vigorously for 0.5 hour, mixed with an equal volume (150 ml) of cetyltrimethylammonium hydroxide solution prepared as in Example 1 and reacted at 100° C. for 168 hours. The mixture had the following composition in terms of moles per mole $Al_2O_3$:

1.1 moles Na₂O 30.6 moles SiO₂

3.0 moles (TEA)₂O 3.25 moles (CTMA)₂O 609 moles H₂O

The resulting solid product was recovered by filtration, washed with water then calcined at 540° C. for 16 hours in air. The calcined product proved to have a surface area of 1352 m²/g and the following equilibrium adsorption capacities in grams/100 grams:

| | |
|---|---|
| H₂O | 23.6 |
| Cyclohexane | >50 |
| n-Hexane | 49 |
| Benzene | 67.5 |

The X-ray diffraction pattern of the calcined product may be characterized as including a very strong relative intensity line at 38.5±2.0 Å d-spacing and a weak line at 20.3±1.0 Å. TEM indicated that the product contained the ultra-large pore material.

EXAMPLE 12

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 24 hours. The mixture had a composition in terms of moles per mole Al₂O₃:

1.25 moles Na₂O 27.8 moles SiO₂

5.1 moles (CTMA)₂O 4.40 moles (TMA)₂O 650 moles H₂O

The resulting solid product was recovered by filtration and dried in air at ambient temperature. The product was then calcined at 540° C. for 1 hour in nitrogen, followed by 6 hours in air. TEM indicated that this product contained the ultra-large pore material. The X-ray diffraction pattern of the calcined product of this example can be characterized as including a very strong relative intensity line at 44.2±2.0 Å d-spacing and weak lines at 25.2±1.5 and 22.0±1.0 Å.

The calcined product proved to have a surface area of 932 m²/g and the following equilibrium adsorption capacities in grams/100 grams:

| | |
|---|---|
| H₂O | 39.3 |
| Cyclohexane | 46.6 |
| n-Hexane | 37.5 |
| Benzene | 50 |

EXAMPLE 13

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a steam box at 100° C. for 48 hours. The mixture had a composition in terms of moles per mole Al₂O₃:

1.25 moles Na₂O 27.8 moles SiO₂

5.1 moles (CTMA)₂O 4.4 moles (TMA)₂O 650 moles H₂O

The resulting solid product was recovered by filtration and dried in air at ambient temperature. The product was then calcined at 540° C. for 1 hour in nitrogen, followed by 6 hours in air. The calcined product proved to have the following equilibrium adsorption capacities in grams/100 grams:

| | |
|---|---|
| H₂O | 35.2 |
| Cyclohexane | >50 |
| n-Hexane | 40.8 |
| Benzene | 53.5 |

The X-ray diffraction pattern of the calcined product may be characterized as including a very strong relative intensity line at 39.1±2.0 Å d-spacing and weak lines at 22.4±1.0 and 19.4±1.0 Å. TEM indicated that this product contained the ultra-large pore material.

EXAMPLE 14

A mixture of 125 grams of 29% CTMA chloride aqueous solution, 200 grams of water, 3 grams of sodium aluminate (in 50 grams H₂O), 65 grams of Ultrasil, amorphous precipitated silica available from PQ Corporation, and 21 grams NaOH (in 50 grams H₂O) was stirred thoroughly and crystallized at 150° C. for 168 hours. The reaction mixture had the following relative molar composition in terms of moles per mole silica:

0.10 moles (CTMA)₂O 21.89 moles H₂O 0.036 moles NaAlO₂

0.53 moles NaOH

The solid product was isolated by filtration, washed with water, dried for 16 hours at room temperature and calcined at 540° C. for 10 hours in air. The calcined product proved to have a surface area of 840 m²/g, and the following equilibrium adsorption capacities in grams/100 grams:

| | |
|---|---|
| H$_2$O | 15.2 |
| Cyclohexane | 42.0 |
| n-Hexane | 26.5 |
| Benzene | 62 |

The X-ray diffraction pattern of the calcined product may be characterized as including a very strong relative intensity line at 40.5±2.0 Å d-spacing. TEM indicated that the product contained the ultra-large pore material.

EXAMPLE 15

To make the primary template mixture for this example, 240 grams of water was added to a 92 gram solution of 50% dodecyltrimethylammonium hydroxide, 36% isopropyl alcohol and 14% water such that the mole ratio of Solvent/R$_2$/O was 155. The mole ratio of H$_2$O/R$_2$/O in this mixture was 149 and the IPA/R$_2$/O mole ratio was 6. To the primary template mixture was added 4.15 grams of sodium aluminate, 25 grams of HiSil, 100 grams of aqueous tetramethylammonium silicate solution (10% SiO$_2$) and 13.2 grams of 25% aqueous tetramethylammonium hydroxide solution. The mole ratio of R$_2$/O/(SiO$_2$+Al$_2$O$_3$) was 0.28 for the mixture.

This mixture was stirred at 25° C. for 1 hour. The resulting mixture was then placed in an autoclave at 100° C. and stirred at 100 rpm for 24 hours. The mixture in the autoclave had the following relative molar composition in terms of moles per mole SiO$_2$:

0.05 mole Na$_2$O 0.036 mole Al$_2$O$_3$ 0.18 mole (C$_{12}$TMA)$_2$O 0.12 mole (TMA)$_2$O 36.0 moles H$_2$O 1.0 mole IPA The resulting solid product was recovered by filtration, washed with water and dried in air at ambient temperature. The product was then calcined at 540° C. for 1 hour in nitrogen, followed by 6 hours in air.

The calcined product proved to have a surface area of 1223 m$^2$/g and the following equilibrium adsorption capacities in grams/100 grams:

| | |
|---|---|
| H$_2$O | 25.5 |
| Cyclohexane | 41.1 |
| n-Hexane | 35.1 |
| Benzene | 51 |

The X-ray diffraction pattern of the calcined product may be characterized as including a very strong relative intensity line at 30.8±1.5 Å d-spacing and weak lines at 17.9±1.0 and 15.5±1.0 Å. TEM indicated this product to contain the ultra-large pore material.

EXAMPLE 16

A 50.75 gram quantity of decyltrimethylammonium hydroxide (prepared by contacting a ca. 29 wt. % solution of decyltrimethylammonium bromide with a hydroxide-for-halide exchange resin) was combined with 8.75 grams of tetraethylorthosilicate. The mixture was stirred for about 1 hour and then transferred to a polypropylene jar which was then placed in a steambox for about 24 hours. The mixture had a composition in terms of moles per mole SiO$_2$:

0.81 mole (C$_{10}$TMA)$_2$O 47.6 moles H$_2$O

The resulting solid product was filtered and washed several times with warm (60-70° C.) distilled water and with acetone. The final product was calcined to 538° C. in N$_2$/air mixture and then held in air for about 8 hours. The calcined product proved to have a surface area of 915 m$^2$/g and an equilibrium benzene adsorption capacity of 35 grams/100 grams. Argon physisorption data indicated an argon uptake of 0.34 cc/gram, and a pore size of 15 Å.

The X-ray diffraction pattern of the calcined product of this example may be characterized as including a very strong relative intensity line at 27.5±1.5 Å d-spacing and weak lines at 15.8±1.0 and 13.7±1.0 Å. TEM indicated that the product of this example contained the ultra-large pore material.

EXAMPLE 17

To eighty grams of cetyltrimethylammonium hydroxide (CTMAOH) solution prepared as in Example 1 was added 1.65 grams of NaAlO$_2$. The mixture was stirred at room temperature until the NaAlO$_2$ was dissolved. To this solution was added 40 grams of aqueous tetramethylammonium (TMA) silicate solution (10 wt. % SiO$_2$), 10 grams of HiSil, 200 grams of water and 70 grams of 1,3,5-trimethylbenzene (mesitylene). The resulting mixture was stirred at room temperature for several minutes. The gel was then loaded into a 600 cc autoclave and heated at 105° C. for sixty-eight hours with stirring at 150 rpm. The mixture had a composition in terms of moles per mole Al$_2$O$_3$:

1 25 moles Na$_2$O 27.8 moles SiO$_2$ 5.1 moles (CTMA)$_2$O 2.24 moles (TMA)$_2$O 2256 moles H$_2$O 80.53 moles 1,3,5-trimethylbenzene The resulting product was filtered and washed several times with warm (60-70° C.) distilled water and with acetone. The final product was calcined to 538° C. in N$_2$/air mixture and then held in air for about 10 hours. The calcined product proved to have an equilibrium benzene adsorption capacity of >25 grams/100 grams.

The X-ray diffraction pattern of the calcined product may be characterized as including a broad, very strong relative intensity line at about 102 Å d-spacing, but accurate positions of lines in the extreme low angle region of the X-ray diffraction pattern are very difficult to determine with conventional X-ray diffractometers. Furthermore, finer collimating slits were required to resolve a peak at this low 2-theta angle. The slits used in this example, starting at the X-ray tube, were 0.1, 0.3, 0.5 and 0.2 mm, respectively. TEM indicated that the product of this example contained several materials with different $d_{100}$ values as observed in their electron diffraction patterns. These materials were found to possess $d_{100}$ values between about 85 Å d-spacing and about 120 Å d-spacing.

EXAMPLE 18

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 120 grams of 1,3,5-trimethylbenzene (mesitylene). The resulting mixture was stirred at room temperature for several minutes. The gel was then loaded into a 600 cc autoclave and heated at 105° C. for ninety hours with stirring at 150 rpm. The mixture had a composition in terms of moles per mole $Al_2O_3$:

1.25 moles $Na_2O$ 27.8 moles $SiO_2$ 5.1 moles $(CTMA)_2O$ 2.24 moles $(TMA)_2O$ 2256 moles $H_2O$ 132.7 moles 1,3,5-trimethylbenzene The resulting product was filtered and washed several times with warm (60–70° C.) distilled water and with acetone. The final product was calcined to 538° C. in $N_2$/air mixture and then held in air for about 10 hours. The calcined product proved to have a surface area of 915 $m^2$/g and an equilibrium benzene adsorption capacity of >25 grams/100 grams. Argon physisorption data indicated an argon uptake of 0.95 cc/gram, and a pore size centered on 78 Å (Dollimore-Heal Method, see Example 22(b)), but running from 70 to greater than 105 Angstoms. The X-ray diffraction pattern of the calcined product of this example may be characterized as having only enhanced scattered intensity in the very low angle region of the X-ray diffraction, where intensity from the transmitted incident X-ray beam is usually observed. However, TEM indicated that the product contained several materials with different $d_{100}$ values as observed in their electron diffraction patterns. These materials were found to possess $d_{100}$ values between about 85 Å d-spacing and about 110 Å d-spacing.

EXAMPLE 19

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, and 18 grams of 1,3,5-trimethylbenzene (mesitylene). The resulting mixture was stirred at room temperature for several minutes. The gel was then loaded into a 300 cc autoclave and heated at 105° C. for four hours with stirring at 150 rpm.

The mixture had a composition in terms of moles per mole $Al_2O_3$:

1.25 moles $Na_2O$ 27.8 moles $SiO_2$ 5.1 moles $(CTMA)_2O$ 2.24 moles $(TMA)_2O$ 650 moles $H_2O$ 19.9 moles 1,3,5-trimethylbenzene The resulting product was filtered and washed several times with warm (60–70° C.) distilled water and with acetone. The final product was calcined to 538° C. in $N_2$/air mixture and then held in air for about 8 hours.

The calcined product proved to have a surface area of 975 $m^2$/g and an equilibrium benzene adsorption capacity of >40 grams/100 grams. Argon physisorption data indicated an argon uptake of 0.97 cc/gram, and a pore size of 63 Å (Dollimore-Heal Method), with the peak occurring at $P/P_o = 0.65$.

The X-ray diffraction pattern of the calcined product of this example may be characterized as including a very strong relative intensity line at 63±5 Å d-spacing and weak lines at 36.4±2.0, 31.3±1.5 Å and 23.8±1.0 Å d-spacing. TEM indicated that the product of this example contained the ultra-large pore material.

EXAMPLE 20

Argon Physisorption Determination

To determine the pore diameters of the mesoporous products with pores up to about 60 Å in diameter, 0.2 gram samples of the products of Examples 1 through 17 were placed in glass sample tubes and attached to a physisorption apparatus as described in U.S. Pat. No. 4,762,010.

The samples were heated to 300° C. for 3 hours in vacuo to remove adsorbed water. Thereafter, the samples were cooled to ° 87K. by immersion of the sample tubes in liquid argon. Metered amounts of gaseous argon were then admitted to the samples in stepwise manner as described in U.S. Pat. No. 4,762,010, column 20. From the amount of argon admitted to the samples and the amount of argon left in the gas space above the samples, the amount of argon adsorbed can be calculated. For this calculation, the ideal gas law and the calibrated sample volumes were used. (See also S. J. Gregg et al., *Adsorption, Surface Area and Porosity*, 2nd ed., Academic Press, 1982). In each instance, a graph of the amount adsorbed versus the relative pressure above the sample, at equilibrium, constitutes the adsorption isotherm. It is common to use relative pressures which are obtained by forming the ratio of the equilibrium pressure and the vapor pressure $P_o$ of the adsorbate at the temperature where the isotherm is measured. Sufficiently small amounts of argon were admitted in each step to generate 168 data points in the relative pressure range from 0 to 0.6. At least about 100 points are required to define the isotherm with sufficient detail.

The step (inflection) in the isotherm, indicates filling of a pore system. The size of the step indicates the amount adsorbed, whereas the position of the step in terms of $P/P_o$ reflects the size of the pores in which the adsorption takes place. Larger pores are filled at higher P/P$_o$. In order to better locate the position of the step in the isotherm, the derivative with respect to log (P/P$_o$) is formed. The adsorption peak (stated in terms of log (P/P$_o$)) may be related to the physical pore diameter (Å) by the following formula:

$$\log(P/P_o) = \frac{K}{d - 0.38} \left[ \frac{S^4}{3(L - D/2)^3} - \frac{S^{10}}{9(L - D/2)^9} - \frac{S^4}{3(D/2)^3} + \frac{S^{10}}{9(D/2)^9} \right]$$

where d=pore diameter in nanometers, K=32.17, S=0.2446, L=d+0.19, and D=0.57.

This formula is derived from the method of Horvath and Kawazoe (G. Horvath et al., *J. Chem. Eng. Japan*, 16 (6) 470(1983)). The constants required for the implementation of this formula were determined from a measured isotherm of ALPO-5 and its known pore size. This method is particularly useful for microporous materials having pores of up to about 60 Å in diameter.

The results of this procedure for the samples from Examples 1 through 16 are tabulated below. The samples from Examples 10, 13 and 15 gave two separate peaks, believed to be the result of two separate ultra-large pore phases in the products.

| Examples | Pore Diameter, Å |
|---|---|
| 1 | 32.2 |
| 2 | 35.4 |
| 3 | 42.5 |
| 4 | 39.6 |
| 5 | 16.9 |
| 6 | 27.3 |
| 7 | 36.6 |
| 8 | 42.6 |
| 9 | 28.3 |
| 10 | 22.8, 30.8 |
| 11 | 36.8 |
| 12 | 36.1 |
| 13 | 35.0, 42.1 |
| 14 | 40.0 |
| 15 | 22.4, 30.4 |
| 16 | 15.0 |

By way of comparison, a commercially prepared sample of zeolite USY (equilibrium benzene sorption capacity of 20.7 grams/100 grams, X-ray diffraction pattern with all the lines of zeolite Y and with the highest d-spacing at about 14 Å) had a pore diameter of about 8.3 Å as determined by the above method.

The method of Horvath and Kawazoe for determining pore size from physisorption isotherms was intended to be applied to pore systems of up to 20 Å diameter; but with some care as above detailed, its use can be extended to pores of up to 60 Å diameter.

In the pore regime above 60 Å diameter, the Kelvin equation can be applied. It is usually given as:

$$\ln(P/P_o) = \frac{-2\gamma V}{r_k RT} \cos\theta$$

where:
$\gamma$=surface tension of sorbate
V=molar volume of sorbate
$\theta$=contact angle (usually taken for practical reasons to be 0)
R=gas constant
T=absolute temperature
$r_k$=capillary condensate (pore) radius
P/P$_o$=relative pressure (taken from the physisorption isotherm)

The Kelvin equation treats adsorption in pore systems as a capillary condensation phenomenon and relates the pressure at which adsorption takes place to the pore diameter through the surface tension and contact angle of the adsorbate (in this case, argon). The principles upon which the Kelvin equation are based are valid for pores in the size range 50 to 1000 Angstrom diameter. Below this range the equation no longer reflects physical reality, since true capillary condensation cannot occur in smaller pores; above this range the logarithmic nature of the equation precludes obtaining sufficient accuracy for pore size determination.

The particular implementation of the Kelvin equation often chosen for measurement of pore size is that reported by Dollimore and Heal (D. Dollimore and G. R. Heal, *J. Applied Chem*, 14, 108 (1964)). This method corrects for the effects of the surface layer of adsorbate on the pore wall, of which the Kelvin equation proper does not take account, and thus provides a more accurate measurement of pore diameter. While the method of Dollimore and Heal was derived for use on desorption isotherms, it can be applied equally well to adsorption isotherms by simply inverting the data set.

Transmission Electron Microscopy

In order to illuminate the microstructure of materials by transmission electromicroscopy (TEM), samples must be thin enough for an electron beam to pass through them, generally about 500–1000 Å or so thick. The crystal morphology of the present materials usually required that they be prepared for study by ultramicrotomy. While time consuming, this technique of sample preparation is quite familiar to those skilled in the art of electron microscopy. The materials are embedded in a resin, in this case a commercially available low viscosity acrylic resin L. R. WHITE (hard), which is then cured at about 80° C. for about 1½ hours. Thin sections of the block are cut on an ultramicrotome using a diamond knife and sections in the thickness range 500–1000 Å are collected on fine mesh electron microscope support grids. For these materials, an LKB model microtome with a 45° C. diamond knife edge was used; the support grids were 400 mesh copper grids. After evaporation of a thin carbon coating on the sample to prevent charging in the microscope (light gray color on a white sheet of paper next to the sample in the evaporator), the samples are ready for examination in the TEM.

High resolution TEM micrographs show projections of structure along the direction that the sample is viewed. For this reason, it is necessary to have a sample in specific orientations to see certain details of the microstructure of the material. For crystalline materials, these orientations are most easily chosen by observing the electron diffraction pattern (EDP) that is produced simultaneously with the electron microscope image. Such EDPs are readily produced on modern TEM instruments using, e.g. the selected area field limiting aperture technique familiar to those skilled in the art of electron microscopy. When an EDP with the desired arrangement of diffraction spots is observed, the corresponding image of the crystal giving that EDP will reveal details of the microstructure along the direction of projection indicated by the EDP. In this way, different projections of a crystal's structure can be observed and identified using TEM.

In order to observe the salient features of the crystalline product of the present invention, it is necessary to view the material in an orientation wherein the corresponding EDP gives a hexagonal arrangement of diffraction spots from a single individual crystal. If multiple crystals are present within the field limiting aperture, overlapping diffraction patterns will occur that can be quite difficult to interpret. The number of diffraction spots observed depends to a degree upon the regularity of the crystalline arrangement in the material, among other things. At the very least the inner ring of bright spots should be observed to obtain a good image. Individual crystals can be manipulated by specimen tilt adjustments on the TEM until this orientation is achieved. More often, it is easier to take advantage of the fact that the specimen contains many randomly oriented crystals and to simply search through the sample until a crystal giving the desired EDP (and hence orientation) is located. This latter technique was used to produce the electron micrographs discussed below.

Microtomed samples of materials from the Examples were examined by the techniques described above in a JEOL 200 CX transmission electron microscope operated at 200,000 volts with an effective 2 Å objective aperture in place. The instrument has a point-to-point resolution of 4.5 Å. Other experimental arrangements familiar to one skilled in the art of high resolution (phase contrast) TEM could be used to produce equivalent images provided care is taken to keep the objective lens on the underfocus (weak leans) side of the minimum contrast lens current setting.

EXAMPLE 21

This example illustrates the aromatic alkylation activity of the ultra-large pore size catalyst.

Catalyst Preparation

The following mixture was charged to an autoclave:
9965 g Cetyltrimethylammonium (CTMA) hydroxide solution prepared by contacting a 29 wt. pct. N,N,N-trimethyl-1-hexdecylammonium chloride solution with a hydroxide-for-halide exchange resin,
208 g Sodium aluminate,
492 g Tetramethylammonim silicate (10% aqueous solution),
1245 g Precipitated hydrated silica (HiSil ™)

The mixture was crystallized at 100° C. for 20 hrs. with stirring under autogeneous pressure. The resulting product was recovered by filtration and dried in air at ambient temperature. A sample of the product was calcined at 540° C. in nitrogen and then in air.

The calcined product had a surface area of 1120 m2/g and the following equilibrium absorption capacities in grams/100 grams:

| | |
|---|---|
| H$_2$O | 10.8 |
| Cyclohexane | >50 |
| n-hexane | >50 |
| Benzene | 67 |

This product exhibited a very strong relative intensity line at 38.4+2.0 Angstroms d-spacing, and weak lines at 22.6+1.0, 20.0+1.0, and 15.2+1.0 Å.

A catalyst composed of 100% H-MCM-41 was prepared by pelletizing the MCM-41 produced by this method. The catalyst pellets were calcined successively in nitrogen and air, followed by exchange with ammonium nitrate solution, after which the exchanged, pelletized catalyst was calcined in air.

A naphthalene alkylation reaction was carried out in a 1 l. autoclave using 150 g (0.612 moles) of a C$_{14}$ 1-olefin and 39 g (0.306 moles) of naphthalene with 5.4 g of the MCM-41 catalyst (2.85 wt %) at 400° F. for 6 hours under 50 psig nitrogen pressure. After decanting and filtering the catalyst, the total liquid product was vacuum distilled at 650° F. to obtain a lube range material. For comparison purposes, a USY zeolite catalyst was also evaluated for naphthalene alkylation reaction under identical conditions. A comparison of the catalyst performance is shown in the following table:

TABLE

| Catalyst | MCM-41 | USY |
|---|---|---|
| Conversion, wt % | | |
| $\alpha$-C$_{14}$ = | 90 | 68 |
| Naphthalene | 99 | 99 |
| Product Yield, wt % | | |
| $\alpha$-C$_{14}$ = | 9 | 26 |
| Naphthalene | 1 | 1 |
| Mono-Alkylated Naph. | 28 | 44 |
| Di-Alkylated Naph. | 44 | 29 |
| Tri- & Tetra-Alkylated Naph. | 18 | 0 |
| Lube Yield, wt % | 90 | 73 |
| Lube Properties: | | |
| Pour Point, °F. | −55 | −65 |
| KV @ 40° C., cS | 84.14 | 34.34 |
| KV @ 100° C., cS | 10.19 | 5.58 |
| Viscosity Index | 102 | 98 |

As shown, the ultra-large pore size catalyst achieved a complete conversion of naphthalene similar to the USY catalyst, but had much higher conversion of olefin (90 vs 68 wt %). This is reflected in the increased alkylated naphthalene lube yield obtained with the ultra-large pore size catalyst (90 wt % vs 73 wt %). Consistent with its ultra large pore dimensions, the MCM-41 catalyst promoted the formation of tri- and tetra-alkylated naphthalene products that could not be obtained with a conventional large pore USY catalyst. As a result, the product obtained from the MCM-41 catalyst, containing a higher level of the polyalkylated naphthalenes, has much higher viscosity than that obtained with USY (10.19 vs 5.58 cS @100° C.). In addition to its high viscosity, the polyalkylated naphthalene lubricant has a very low pour point (−50° F.) and high VI (102 VI). The use of a combination of the ultra-large pore materials in combination with conventional alkylation catalysts such as USY therefore has the potential to provide alkylated naphthalene synthetic lubes with a wide range of viscosities, thus providing flexibility in product application.

We claim:

1. A process for preparing long chain alkyl-substituted aromatic compounds which comprises reacting an aromatic compound with an alkylating agent under alkylation reaction conditions in the presence of an alkylation catalyst comprising an inorganic, non-layered, porous, crystalline phase material having pores with diameters of at least about 13 Å and exhibiting, after calcination, an X-ray diffraction pattern with at least one d-spacing greater than about 18 Å with a relative intensity of 100, and having a benzene adsorption capacity of greater than about 15 grams benzene per 100 grams at 50 torr and 25° C., to form an alkylated aromatic compound possessing at least one alkyl group derived from the alkylating agent.

2. A process according to claim 1 in which the crystalline phase material of the alkylation catalyst has, after calcination, a hexagonal arrangement of uniformly-sized pores with diameters of at least about 13 Å and exhibits a hexagonal electron diffraction pattern that can be indexed with a $d_{100}$ value greater than about 18 Å.

3. A process according to claim 1 in which the crystalline phase has an X-ray diffraction pattern following calcination with at least one peak whose d-spacing corresponds to the $d_{100}$ value from the electron diffraction pattern.

4. A process according to claim 1 in which the crystalline phase has a composition expressed as follows:

$$M_{n/q}(W_aX_bY_cZ_dO_h)$$

wherein M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and $(a+b+c+d)=1$.

5. A process according to claim 4 wherein W comprises a divalent first row transition metal or magnesium; X comprises aluminum, boron, gallium or iron; Y comprises silicon or germanium; and Z comprises phosphorus.

6. A process according to claim 5 wherein a and d are 0 and $h=2$.

7. A process according to claim 6 wherein X comprises aluminum, boron, gallium or iron and Y comprises silicon or germanium.

8. A process according to claim 6 wherein X comprises aluminum and Y comprises silicon.

9. A process according to claim 1 in which the alkylation catalyst comprises a mesoporous crystalline aluminosilicate which has, after calcination, a hexagonal arrangement of uniformly-sized pores with diameters of at least about 13 Å and the structure of MCM-41.

10. A process according to claim 1 in which the alkylating aliphatic group contains at least about 6 carbon atoms.

11. A process according to claim 10 in which the alkylating aliphatic group contains at least about 12 carbon atoms.

12. A process according to claim 11 in which the alkylating aliphatic group contains from 14 to 20 carbon atoms.

13. A process according to claim in which the alkylating agent comprises an olefin.

14. A process according to claim 1 in which the alkylation reaction conditions include a temperature of from about 100° C. to about 400° C., a pressure of from about 0.2 to about 25 atmospheres, an WHSV of from about 0.1 to 10 and an alkylatable aromatic compound to alkylating agent mole ratio of from about 0.1:1 to 50:1.

15. A process according to claim 14 in which the alkylation reaction conditions include a temperature of from about 100° C. to 300° C., a pressure of from about 1 to about 5 atmospheres, a WHSV of from about 0.5 to about 5 and an alkylatable aromatic compound to alkylating agent mole ratio of from about 0.5:1 to about 5:1.

16. A process according to claim in which the aromatic compound comprises naphthalene or a substituted naphthalene.

17. A process according to claim in which the aromatic compound comprises naphthalene.

18. A process according to claim 1 in which the catalyst comprises the porous crystalline material and alumina, silica or silca-alumina as a binder.

19. A process according to claim 1 in which the catalyst comprises from 2 to 80 weight percent of the porous crystalline material and alumina, silica or silca-alumina as a binder.

20. A process for preparing long chain alkyl substituted naphthalenes which comprises reacting naphthalene with a olefin containing at least 8 carbon atoms as an alkylating agent under alkylation reaction conditions including a pressure of at least 50 psig, in the presence of an alkylation catalyst comprising a an inorganic, porous, crystalline phase material having a hexagonal arrangement of uniformly-sized pores with diameters of at least about 13 Å which exhibits a hexagonal electron diffraction pattern that can be indexed with a $d_{100}$ value greater than about 18 Å and an X-ray diffraction pattern with at least one d-spacing greater than about 18 Å with a realtive intensity of 100, and having a benzene adsorption capacity of greater than about 15 grams benzene per 100 grams at 50 torr and 25° C., to form an alkylated naphthalene possessing at least one alkyl group derived from the alkylating agent.

21. A process according to claim 20 in which the crystalline phase has an X-ray diffraction pattern following calcination with at least one peak whose d-spacing corresponds to the $d_{100}$ value from the electron diffraction pattern.

22. A process according to claim 20 in which the crystalline phase has a composition expressed as follows:

$$M_{n/q}(W_aX_bY_cZ_dO_h)$$

wherein M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and $(a+b+c+d)=1$.

23. A process according to claim 22 wherein W comprises a divalent first row transition metal or magnesium; X comprises aluminum, boron, gallium or iron; Y comprises silicon or germanium; and Z comprises phosphorus.

24. A process according to claim 23 wherein a and d are 0 and $h=2$.

25. A process according to claim 24 wherein X comprises aluminum, boron, gallium or iron and Y comprises silicon or germanium.

26. A process according to claim 24 wherein X comprises aluminum and Y comprises silicon.

27. A process according to claim 20 in which the alkylation catalyst comprises a mesoporous crystalline aluminosilicate which has, after calcination, a hexagonal arrangement of uniformly-sized pores with diameters of at least about 13 Å and the structure of MCM-41.

28. A process according to claim 20 in which the alkylation reaction conditions include a temperature of from about 100° C. to about 400° C., a pressure of from about 0.2 to about 25 atmospheres.

29. A process according to claim 20 in which the catalyst comprises the porous crystalline material and alumina, silica or silca-alumina as a binder.

30. A process according to claim 29 in which the catalyst comprises from 2 to 80 weight percent of the porous crystalline material and alumina, silica or silca-alumina as a binder.

* * * * *

UNITED STATES PATENT AND TRADEMARK OFFICE
CERTIFICATE OF CORRECTION

PATENT NO. :   5,191,134
DATED      :   March 2, 1993
INVENTOR(S) :  Q.N. Le

It is certified that error appears in the above-identified patent and that said Letters Patent is hereby corrected as shown below:

Col. 31, claim 13, line 55    "claim" should be --claim 1--

Col. 32, claim 16, line 1     "claim" should be --claim 1--

Col. 32, claim 17, line 4     "claim" should be --claim 1--

Signed and Sealed this

Twenty-first Day of December, 1993

Attest:

BRUCE LEHMAN

Attesting Officer    Commissioner of Patents and Trademarks